United States Patent

Ogata et al.

[11] Patent Number: 5,981,530
[45] Date of Patent: *Nov. 9, 1999

[54] PIPERAZINE DERIVATIVE

[75] Inventors: Kazumi Ogata, Toyonaka; Takahiro Sakaue, Itami; Kazuhiko Ito; Hidetoshi Nakao, both of Amagasaki, all of Japan

[73] Assignee: Senju Pharmaceutical Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/622,003

[22] Filed: Mar. 26, 1996

[30] Foreign Application Priority Data

Mar. 29, 1995 [JP] Japan .................... 7-070985

[51] Int. Cl.$^6$ .................... A61K 31/495; C07D 295/08
[52] U.S. Cl. .................... 514/255; 544/360; 544/398
[58] Field of Search .................... 514/253, 255; 544/363, 373, 396, 397, 398

[56] References Cited

U.S. PATENT DOCUMENTS

| | | | |
|---|---|---|---|
| 4,616,086 | 10/1986 | Witte et al. | 544/383 |
| 5,504,087 | 4/1996 | Ogata et al. | 514/253 |

FOREIGN PATENT DOCUMENTS

| | | |
|---|---|---|
| 0 076 996 | 4/1983 | European Pat. Off. . |
| 0 089 634 | 9/1983 | European Pat. Off. . |
| 0 611 748 | 8/1994 | European Pat. Off. . |

Primary Examiner—Jose' G. Dees
Assistant Examiner—Sabiha Qazi
Attorney, Agent, or Firm—Wenderoth, Lind & Ponack, L.L.P.

[57] ABSTRACT

The present invention provides a piperazine derivative of the following formula or a pharmacologically acceptable salt thereof (I)

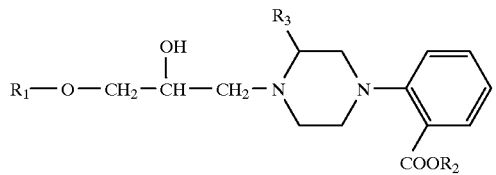

wherein $R_1$ represents a benzene ring, naphthalene ring, quinoline ring, indole ring or chroman ring that may be substituted by lower alkyl, lower alkoxy and/or hydroxy; $R_2$ and $R_3$ independently represent hydrogen or lower alkyl.

The compound of the present invention has potent antiallergic activity and can therefore be used with advantage in the treatment of various allergic diseases.

17 Claims, 3 Drawing Sheets

PIPERAZINE DERIVATIVE

BACKGROUND OF THE INVENTION

1. Field of the Invention

The present invention relates to novel and useful piperazine derivatives, processes for their production, and pharmaceutical compositions and antiallergic compositions comprising said derivatives as active ingredients.

2. Description of the Prior Art

The inventors of the present invention succeeded in synthesizing propanolamine derivatives of the following formula and found that these compounds are of value as antihypertensive and antiglaucoma agents (JP Application H-6-11844).

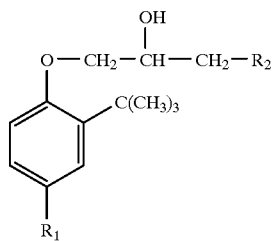

(wherein $R_1$ represents hydrogen, lower alkyl or lower alkoxy; $R_2$ represents isopropylamino, tert-butylamino, 2-(2-methoxyphenyl)ethyl-1-amino, 4-(2-methoxyphenyl)-1-piperazinyl, or 4-piperonyl-1-piperazinyl; provided, however, that where $R_1$ is hydrogen, $R_2$ is neither isopropylamino nor tert-butylamino and that where $R_1$ is methyl, $R_2$ is not isopropylamino).

The inventors of the present invention thence proceeded with further research into the synthesis and pharmacological profile assessment of related compounds. As a result, they synthesized novel piperazine derivatives and discovered that these compounds are of value as antiallergic agents. Based on those findings, the inventors did further research and have perfected the present invention.

SUMMARY OF THE INVENTION

The present invention is thus directed to:

(1) a piperazine derivative of the following formula (I) or a pharmacologically acceptable salt thereof (both the derivative and the salt will hereinafter sometimes be referred to collectively as the compound of the invention).

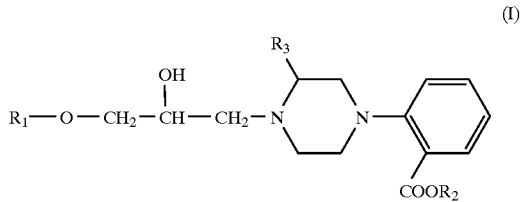

(wherein $R_1$ represents a benzene ring, naphthalene ring, quinoline ring, indole ring or chroman ring that may be substituted by lower alkyl, lower alkoxy and/or hydroxy; $R_2$ and $R_3$ independently represent hydrogen or lower alkyl);

(2) a method of producing the above piperazine derivative or pharmacologically acceptable salt which comprises subjecting a 2,3-epoxypropanol derivative of the following formula (II) (wherein $R_1$ is as defined above) and a 4-(2-carbalkoxyphenyl)piperazine of the following formula (III) (wherein $R_2$ and $R_3$ are as defined above) to thermal condensation reaction or by subjecting the resulting product further to hydrolysis reaction;

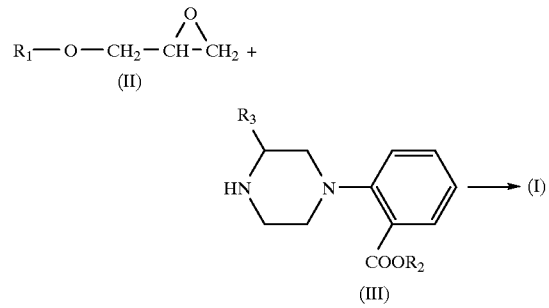

(3) a pharmaceutical composition comprising said piperazine derivative or pharmacologically acceptable salt as an active ingredient.

(4) an antiallergic composition comprising said piperazine derivative or pharmacologically acceptable salt as an active ingredient.

DETAILED DESCRIPTION OF THE INVENTION

Figure 1:
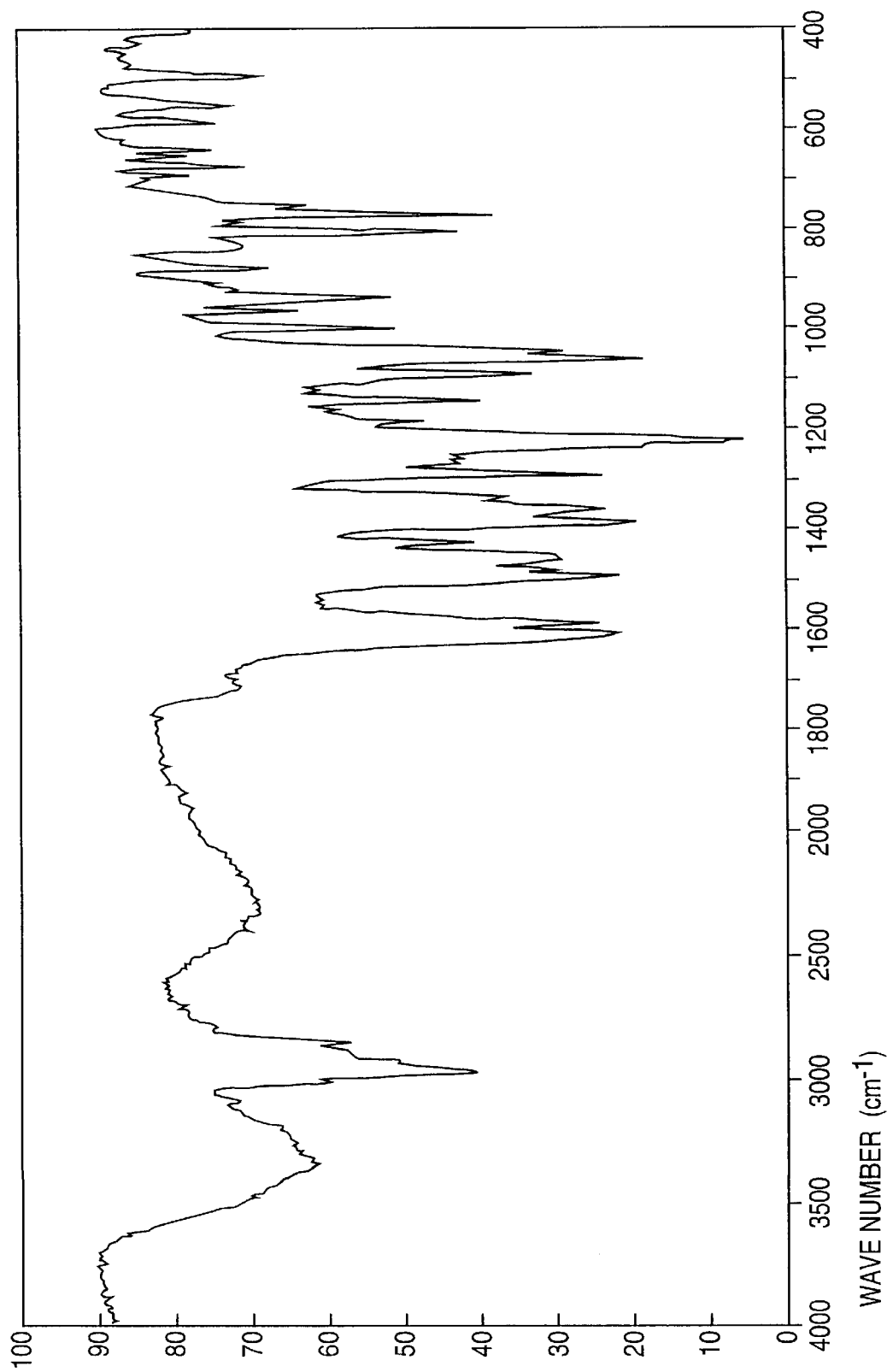
FIG. 1 shows an infrared absorption spectrum (IR) of the compound synthesized in Example 1.
Figure 2:
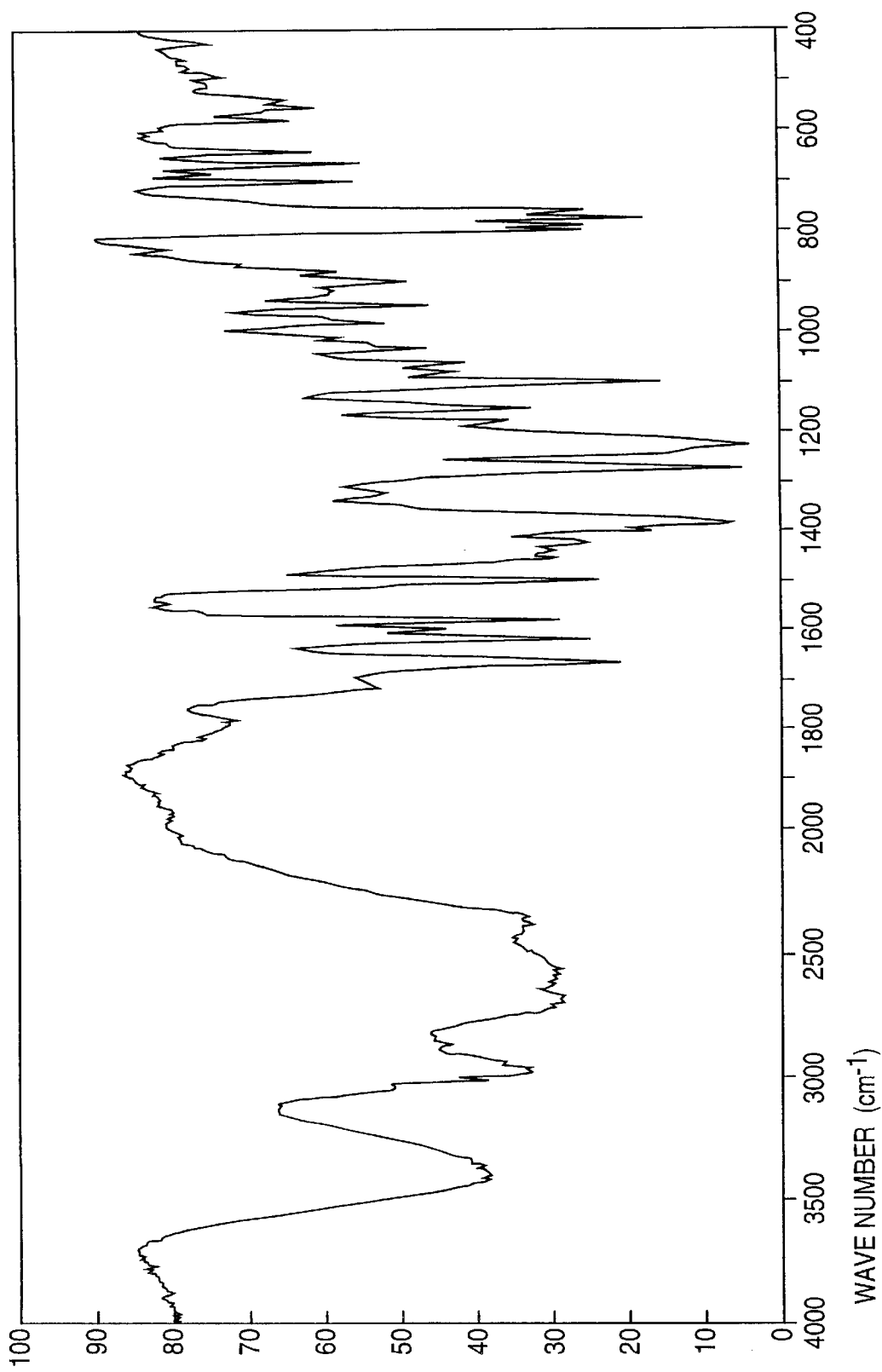
FIG. 2 shows an infrared absorption spectrum (IR) of the compound synthesized in Example 4.
Figure 3:
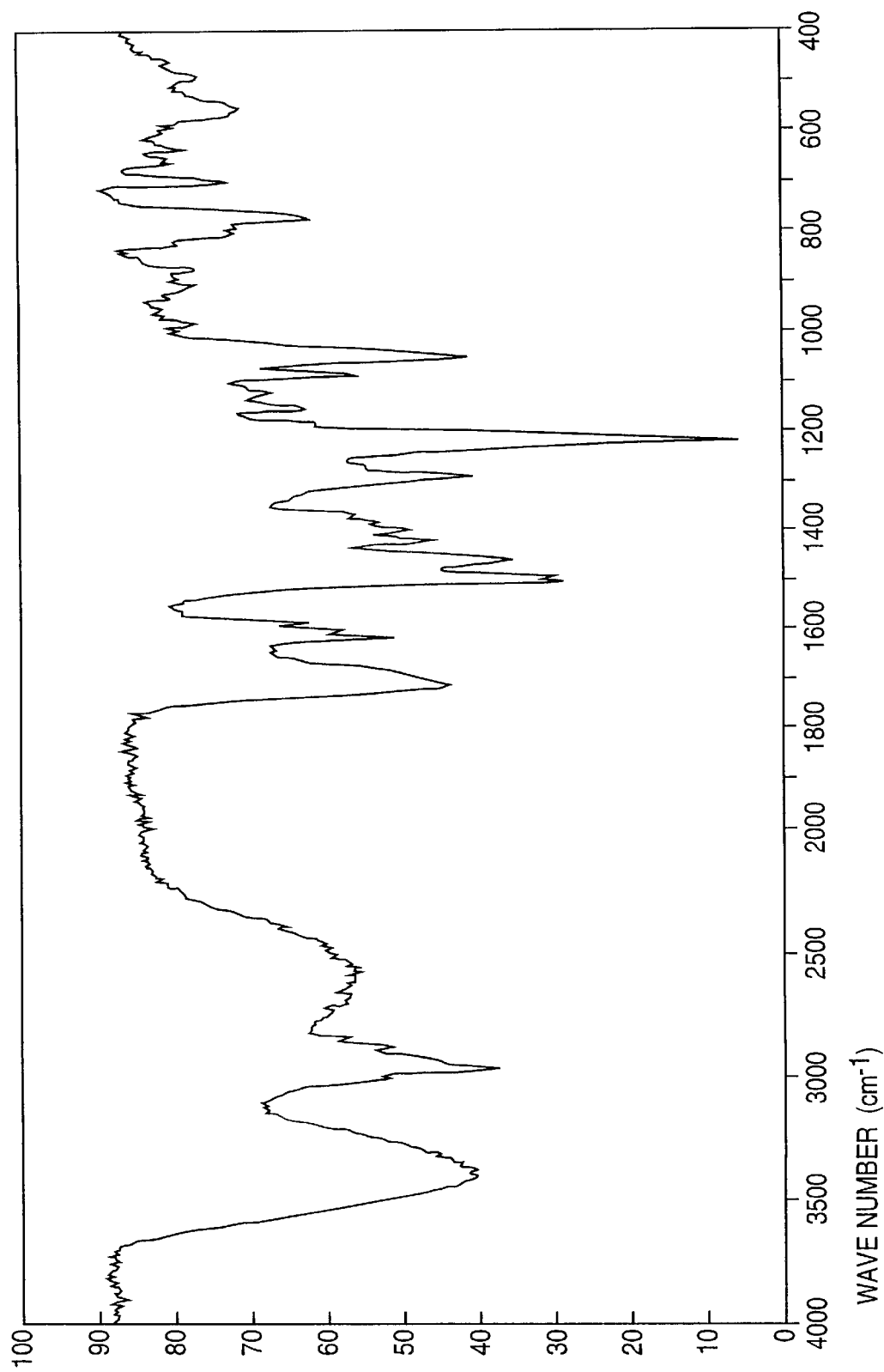
FIG. 3 shows an infrared absorption spectrum (IR) of the compound synthesized in Example 6.

The following specific compounds, inclusive of the corresponding pharmacologically acceptable salts, can be mentioned as typical examples of the compound of the invention.

(1) 3-[4-(2-Carbethoxyphenyl)piperazinyl]-1-(2-tert-butyl-4-methoxyphenoxy)propan-2-ol
(2) 3-[4-(2-Carboxyphenyl)piperazinyl]-1-(2-tert-butyl-4-methoxyphenoxy)propan-2-ol
(3) 3-[4-(2-Carbethoxyphenyl)piperazinyl]-1-(4-hydroxyphenoxy)propan-2-ol
(4) 3-[4-(2-Carboxyphenyl)piperazinyl]-1-(4-hydroxyphenoxy)propan-2-ol
(5) 3-[4-(2-Carbethoxyphenyl)piperazinyl]-1-phenoxypropan-2-ol
(6) 3-[4-(2-Carboxyphenyl)piperazinyl]-1-phenoxypropan-2-ol
(7) 3-[4-(2-Carbethoxyphenyl)piperazinyl]-1-(1-naphthyloxy)propan-2-ol
(8) 3-[4-(2-Carboxyphenyl)piperazinyl]-1-(1-naphthyloxy)propan-2-ol
(9) 3-[4-(2-Carbethoxyphenyl)piperazinyl]-1-(1H-indol-4-yloxy)propan-2-ol
(10) 3-[4-(2-Carboxyphenyl)piperazinyl]-1-(1H-indol-4-yloxy)propan-2-ol
(11) 3-[4-(2-Carboxyethoxyphenyl)-2-methylpiperazinyl]-1-(2-tert-butyl-4-methoxyphenoxy)propan-2-ol
(12) 3-[4-(2-Carboxyphenyl)-2-methylpiperazinyl]-1-(2-tert-butyl-4-methoxyphenoxy)propan-2-ol
(13) 3-[4-(2-Carboxyethoxyphenyl)piperazinyl]-1-(3,4-methylenedioxyphenoxy)propan-2-ol

(14) 3-[4-(2-Carboxyphenyl)piperazinyl]-1-(3,4-methylenedioxyphenoxy)propan-2-ol
(15) 3-[4-(2-Carbethoxyphenyl)piperazinyl]-1-(α-tocopherol-6-yl)propan-2-ol
(16) 3-[4-(2-Carboxyphenyl)piperazinyl]-1-(α-tocopherol-6-yl)propan-2-ol
(17) 3-[4-(2-Carboxyphenyl)piperazinyl]-1-(4-aminophenoxy)propan-2-ol
(18) 3-[4-(2-carboxyphenyl)piperazinyl]-1-(3-tert-butyl-4-hydroxyphenoxy)propan-2-ol The lower alkyl that can be mentioned for $R_2$ and $R_3$ in the above formula includes straight-chain, branched or cyclic alkyl groups of 1 to 5 carbon atoms. Specifically, methyl, ethyl, n-propyl, iso-propyl, cyclo-propyl, n-butyl, tert-butyl, sec-butyl, n-pentyl, 1-ethylpropyl, iso-pentyl, etc. can be mentioned.

The benzene ring, naphthalene ring, quinoline ring, indole ring or chroman ring which is represented by $R_1$ in the formula may be substituted by lower alkyl, lower alkoxy or hydroxy. The lower alkyl here is the same as that defined above. The lower alkoxy on the rings may be straight-chain, branched or cyclic and preferably contains 1 to 5 carbons atoms. Thus, for example, methoxy, ethoxy, propoxy, iso-propoxy, n-butoxy, iso-butoxy, tert-butoxy, n-pentyloxy, neo-pentyloxy, 2-methylbutoxy, 1,2-dimethylpropoxy and 1-ethylpropoxy can be mentioned.

The compound of the invention can be synthesized by reacting a 2,3-epoxypropanol derivative of the following formula (II) with a 4-(2-carbalkoxyphenyl)piperazine of the following formula (III).

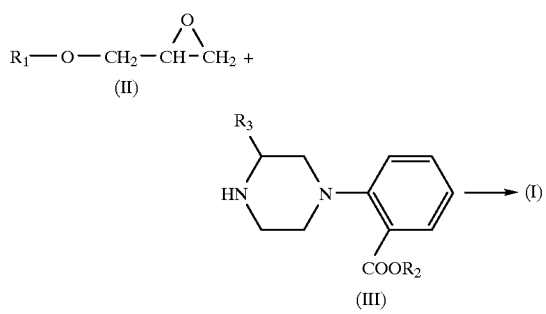

The method of producing the compound of the invention is now described in detail.

The starting material 2,3-epoxypropanol derivative of formula (II) can be synthesized by any known process such as typically the following. Thus, the derivative (II) can be obtained by reacting a compound of the formula $R_1OH$ ($R_1$ is as defined hereinbefore) with a halomethyloxirane of the following formula (X represents halogen such as chlorine, bromine or iodine) under heating in the presence of an alkali carbonate in a solvent such as acetone or methyl ethyl ketone.

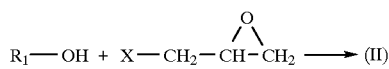

The starting material 4-(2-carbalkoxyphenyl)piperazine of formula (III) can be synthesized by any known process such as typically the following. Thus, the compound (III) can be obtained by reacting N-monobenzylpiperazine with an o-halogenated benzoic acid lower alkyl ester under heating in the presence or absence of a solvent to give the corresponding [1-benzyl-4-(2-carboxyalkyl)]piperazine (IV) and subjecting the same (IV) to catalytic reduction in the presence of a catalyst such as palladium-on-carbon (Pd—C). In the formula, $R_2$ and X are as defined hereinbefore.

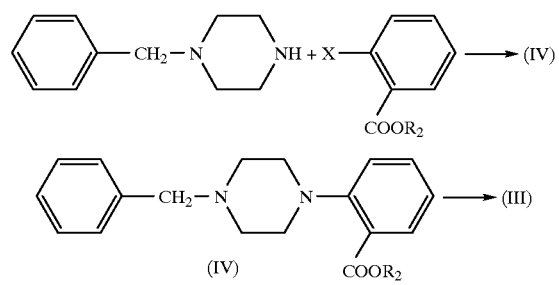

The compound of the invention can be obtained by reacting these compounds (II) and (III) with each other in the presence of an organic amine, e.g. triethylamine, in a solvent such as dioxane at the reflux temperature of the system. Under reflux conditions, this reaction goes to completion in approximately 5–6 hours. The solvent that can be used for this reaction may be virtually any solvent that does not interfere with the reaction, although dioxane can be used with particular advantage. The preferred organic amine is triethylamine, tributylamine or the like. Among species of the compound of the invention, a compound wherein $R_2$ is hydrogen can be obtained by subjecting the corresponding compound wherein $R_2$ is a lower alkyl group to saponification (hydrolysis of the ester) with an alkali such as sodium hydroxide.

The thus-obtained compound of the invention can be converted to a pharmacologically acceptable salt. By way of illustration, such a salt can be obtained by adding an alkali metal or alkaline earth metal ion donor, such as the corresponding hydroxide, carbonate or bicarbonate, to the compound of the invention in a suitable solvent, or by making the reaction mixture acidic with acids. This conversion to a salt can be carried out with or without prior isolation of the substrate compound from the reaction mixture.

The thus-obtained compound of the invention can be purified and isolated by silica gel chromatography or recrystallization from a suitable solvent such as methanol or ethanol.

The compound of the invention is a novel compound never described in published literature before and, because of its potent antiallergic activity, is a very useful compound.

For use in the antiallergic composition of the present invention, the compound of the invention can be whichever of the free compound and a pharmacologically acceptable salt thereof. The pharmacologically acceptable salt is typically any of the alkali metal salts such as the sodium salt and potassium salt or any of the alkaline earth metal salts such as the calcium salt and magnesium salts. The salt also includes inorganic salts such as the hydrochloride, sulfate and nitrate, and organic salts such as the acetate, maleate and tartrate. Any other salts that are pharmacogically acceptable can be used where appropriate.

The allergic disease that can be treated with the antiallergic composition of the present invention includes but is not limited to bronchial asthma, pollinosis, allergic rhinitis, alimentary allergic gastritis, allergic diarrhea, ulcerative colitis, stomatitis, nodular periarteritis, obliterating endarteritis, endocarditis, urticaria, edema, contact dermatitis, phlyctenule, sympathetic ophthalmia, allergic conjunctivitis, and allergic keratitis.

The antiallergic composition of the present invention can be advantageously administered orally or otherwise for the treatment of various allergic diseases such as those mentioned above. As to the dosage form, the composition can be processed by established pharmaceutical procedures into various solid forms such as tablets, granules, powders, capsules, ointments, etc. and various liquid forms such as eye-drops, nose-drops, syrups, etc. These preparations can be supplemented with suitable amounts of additives which are commonly employed, such as the excipient, binder, disintegrator, thickener, dispersant, reabsorption promoter, buffer, surfactant, preservative, isotonizing agent, stabilizer, pH control agent, and so forth.

The dosage for the compound of the invention as an antiallergic agent depends on the species of compound selected, the type of disease to be treated, the patient's body weight and age, the clinical symptom to be managed, and the contemplated therapeutic regimen but taking an injectable dosage form as an example, the recommended daily dose for an adult patient is about 0.1 mg to about 30 mg to be administered once a day. As to oral dosage forms, the recommended dose for an adult patient is about 1 mg to about 100 mg, which is to be administered a few times daily. As a topical ophthalmic dosage form, a few drops of a solution or suspension of about 0.01 (w/v) %–0.5 (w/v) % concentration can be advantageously instilled in the eye several times a day.

Depending on the objective and need, the antiallergic composition of the present invention may contain two or more species of the compound of the invention.

EXAMPLES

The following examples and formulation examples are intended to describe the present invention in further detail.

Reference Example 1
Ethyl 2-piperazinylbenzoate monoacetate

A mixture of ethyl 2-bromobenzoate (11.5 g), N-monobenzylpiperazine (17.6 g), and potassium carbonate (6.91 g) is stirred at 220° C. for 2 hours. After cooling, the reaction mixture is extracted with ethyl acetate. This extract is washed serially with water and saturated aqueous NaCl solution and dried over anhydrous sodium sulfate. The solvent is then distilled off and the residue is subjected to silica gel chromatography using ethyl acetate-hexane (1:3) to give a colorless oil (10.5 g). This oil (10.5 g) is subjected to catalytic reduction at atmospheric pressure for 12 hours using 2.5 g of 10% palladium-on-carbon and, as the reaction solvent, a mixture of acetic acid (100 ml), dioxane (100 ml) and water (50 ml) to provide ethyl 2-piperazinylbenzoate monoacetate (8.0 g).

Reference Example 2
2-Tert-butyl-4-methoxyphenoxymethyloxirane

4-Hydroxy-3-tert-butylanisole (4.5 g, 0.025 mol) and chloromethyloxirane (8.0 g) are dissolved in methyl ethyl ketone (150 ml), and following addition of anhydrous potassium carbonate (7.0 g), the mixture is refluxed for 8 hours. The inorganic salt formed is filtered off and the filtrate is concentrated. The oily residue is extracted with ethyl acetate and washed serially with 1% NaOH solution and water. The ethyl acetate is then distilled off to provide 2-tert-butyl-4-methoxyphenoxymethyloxirane as oil (ca 5 g).

Example 1
3-[4-(2-Carboxyphenyl)piperazinyl]-1-(2-tert-butyl-4-methoxyphenoxy)propan-2-ol Ethyl 2-piperazinylbenzoate monoacetate (2.94 g) as obtained in Reference Example 1 and 2-tert-butyl-4-methoxyphenoxymethyloxirane (2.36 g) as obtained in Reference Example 2 are dissolved in dioxane (100 ml). To this solution is added triethylamine (1.7 ml) dropwise and the mixture is refluxed for 6 hours. The solvent is then distilled off and the residue is extracted with ethyl acetate. The extract is washed with diluted hydrochloric acid, water, and saturated aqueous NaCl solution in that order and dried over anhydrous sodium sulfate. After the solvent is distilled off, the residue is recrystallized from benzene-iso-propyl ether to give 3-[4-(2-carbethoxyphenyl)-piperazinyl]-1-(2-tert-butyl-4-methoxyphenoxy)propan-2-ol (2.5 g). This product (2.0 g) is refluxed for 3 hours in 2N-sodium hydroxide (30 ml)-ethanol (10 ml) and, then, neutralized with acetic acid. The solvent is then distilled off and the residue is dissolved in ethanol. To this solution is added water and the resulting crystals are collected by filtration to provide the title compound melting at 171° C.–172° C. (1.7 g).

Elemental analysis for $C_{25}H_{34}N_2O_5$; Calcd. (%): C, 67.85; H, 7.74; N, 6.33; Found (%): C, 67.78; H, 7.71; N, 6.38

Example 2
3-[4-(2-Carboxyphenyl)piperazinyl]-1-(4-hydroxyphenoxy)propan-2-ol A mixture of ethyl 2-piperazinylbenzoate monoacetate (1.54 g) as obtained in Reference Example 1, 4-benzyloxyphenoxymethyloxirane (2.97 g) as obtained by the same reaction procedure as described in Reference Example 2, dioxane (50 ml), and triethylamine (1.7 ml) is refluxed for 5 hours. This reaction mixture is treated as in Example 1 and the residue is subjected to silica gel chromatography using chloroform to give 3-[4-(2-carbethoxyphenyl)piperazinyl]-1-(4-benzyloxyphenoxy)propan-2-ol (2.6 g) as colorless oil. This compound (2.6 g) is subjected to catalytic reduction at atmospheric pressure using 10% palladium-on-carbon (1.5 g) in dioxane (80 ml)-water (20 ml) to give 3-[4-(2-carbethoxyphenyl)piperazinyl]-1-(4-hydroxyphenoxy)propan-2-ol (1.6 g). This compound (1.2 g) is hydrolyzed and after-treated as in Example 1 and the residue is converted to the hydrochloride and recrystallized from ethanol to provide the title compound melting at 235° C.–237° C. (1.0 g).

Elemental analysis for $C_{20}H_{24}N_2O_5 \cdot HCl$; Calcd. (%): C, 58.75; H, 6.16; N, 6.85; Found (%): C, 58.55; H, 6.15; N, 7.02

Example 3
3-[4-(2-Carboxyphenyl) piperazinyl]-1-phenoxypropan-2-ol

A mixture of ethyl 2-piperazinylbenzoate monoacetate (2.94 g) as obtained in Reference Example 1, phenoxymethyloxirane (1.5 g) as obtained by the same reaction procedure in Reference Example 2, triethylamine (1.7 ml), and dioxane (80 ml) is refluxed for 5 hours. This reaction mixture is treated as in Example 1 and the residue is subjected to silica gel chromatography using ethyl acetate-hexane (1:2) to give 3-[4-(2-carbethoxyphenyl)piperazinyl]-1-phenoxypropan-2-ol as light-yellow oil (2.8 g). This compound (2.0 g) is hydrolyzed and worked up as in Example 1 and the residue is converted to the hydrochloride and recrystallized from methanol to provide the title compound melting at 235° C.–237° C. (1.6 g).

Elemental analysis for $C_{20}H_{24}N_2O_4 \cdot HCl$; Calcd. (%): C, 61.14; H, 6.41; N, 7.13; Found (%): C, 61.12; H, 6.40; N, 6.99

Example 4

3-[4-(2-Carboxyphenyl)piperazinyl]-1-(1-naphthyloxy)propan-2-ol

A mixture of ethyl 2-piperazinylbenzoate monoacetate (1.47 g) as obtained in Reference Example 1, 1-naphthyloxymethyloxirane (1.0 g) as obtained by the same reaction procedure as described in Reference Example 2, triethylamine (0.8 ml), and dioxane (50 ml) is refluxed for 4 hours. This reaction mixture is treated as in Example 1 and the residue is subjected to silica gel chromatography using ethyl acetate-hexane (1:3) to give 3-[4-(2-carbethoxyphenyl)piperazinyl]-1-(1-naphthyloxy)propan-2-ol (1.3 g) as brown oil. This compound (1.3 g) is hydrolyzed and worked up as in Example 1. After conversion to the hydrochloride, the product is dissolved in methanol and the crystals separating out on addition of ether are collected by filtration to provide the title compound melting at 215° C.–218° C. (0.9 g).

Elemental analysis for $C_{24}H_{26}N_2O_4 \cdot 2HCl$; Calcd. (%): C, 60.13; H, 5.89; N, 5.84; Found (%): C, 60.42; H, 6.00; N, 5.70

Example 5

3-[4-(2-Carboxyphenyl)piperazinyl]-1-(1H-indol-4-yloxy)propan-2-ol

A mixture of ethyl 2-piperazinylbenzoate monoacetate (2.34 g) as obtained in Reference Example 1, 4-(2,3-epoxypropoxy)indole (1.89 g) as obtained by the same reaction procedure as described in Reference Example 2, and dioxane (50 ml) was treated in the same manner as Example 1 to give 3-[4-(2-carbethoxyphenyl)piperazinyl]-1-(1H-indol-4-yloxy)propan-2-ol (2.58 g). This compound (2.58 g) is hydrolyzed and treated as in Example 1 and the residue is purified by silica gel chromatography to provide the title compound melting at 163° C.–165° C. (1.25 g).

Elemental analysis for $C_{22}H_{25}N_3O_4$; Calcd. (%): C, 66.82; H, 6.37; N, 10.63; Found (%): C, 66.73; H, 6.27; N, 10.46

Example 6

3-[4-(2-Carboxyphenyl)-2-methylpiperazinyl]-1-(2-tert-butyl-4-methoxyphenoxy)propan-2-ol Using 2-bromobenzoic acid (6.87 g), 2-methylpiperazine (6.01 g), and potassium carbonate (4.15 g), the reaction procedure of Reference Example 1 is repeated to give 3-[4-(2-carboxyethoxyphenoxy)-2-methylpiperazinyl]-1-(2-tert-butyl-4-methoxyphenyl)propan-2-ol as yellow oil (8.8 g). A mixture of this oil (3.08 g), 2-tert-butyl-4-methoxyphenoxymethyloxirane (2.36 g) as obtained in Reference Example 2, triethylamine (2.8 ml), and dioxane (100 ml) is refluxed for 5 hours. Thereafter, the reaction mixture is hydrolyzed and worked up to provide the title compound melting at 205° C.–208° C. (0.7 g).

Elemental analysis for $C_{26}H_{36}N_2O_5 \cdot 2HCl \cdot 1/2H_2O$; Calcd. (%): C, 57.99; H, 7.30; N, 5.20; Found (%): C, 58.22; H, 7.09; N, 5.11

Example 7

3-[4-(2-Carboxyphenyl)piperazinyl]-1-(3,4-methylenedioxyphenoxy)propan-2-ol

A mixture of ethyl 2-piperazinylbenzoate monoacetate (2.5 g) as obtained in Reference Example 1, 3,4-methylenedioxyphenoxyoxirane (1.94 g) as obtained by the same reaction procedure as described in Reference Example 1, dioxane (90 ml), and triethylamine (1.7 ml) is refluxed for 5 hours. This reaction mixture is treated as in Example 1 and the residue is subjected to silica gel chromatography using ethyl acetate-hexane (1:1) to provide 3-[4-(2-carbethoxyphenyl)piperazinyl]-1-(3,4-methylenedioxyphenoxy)propan-2-ol (2.6 g) as light-brown oil. This product (2.0 g) is hydrolyzed and treated as in Example 1 and the residue is converted to the hydrochloride and recrystallized from ethanol to provide the title compound melting at 229° C.–231° C. (1.6 g).

Elemental analysis for $C_{21}H_{24}N_2O_6 \cdot HCl$; Calcd. (%): C, 57.73; H, 5.77; N, 6.41; Found (%): C, 57.68; H, 5.76; N, 6.36

Example 8

3-[4-(2-carboxyphenyl)piperazinyl]-1-(α-tocopherol-6-yl)propan-2-ol

A mixture of ethyl 2-piperazinylbenzoate monoacetate 2.94 g) as obtained in Reference Example 1, α-tocopheroloxirane (4.87 g) as obtained by the same reaction procedure as described in Reference Example 2, dioxane (100 ml), and triethylamine (1.8 ml) is refluxed for 4 hours. This reaction mixture is treated as in Example 1 and the residue is subjected to silica gel chromatography using ethyl acetate-hexane (1:2) to provide 3-[4-(2-carbethoxyphenyl)piperazinyl]-1-(α-tocopherol-6-yl)propan-2-ol (2.5 g) as yellowish-brown oil. This product (2.2 g) is hydrolyzed and treated as in Example 1 and recrystallized from ethanol-water to provide the title compound melting at 94° C.–96° C. (1.4 g).

Elemental analysis for $C_{43}H_{68}N_2O_5$; Calcd. (%): C, 74.52; H, 9.89; N, 4.04; Found (%): C, 74.22; H, 10.08; N, 3.97

Example 9

3-[4-(2-carboxyphenyl)piperazinyl]-1-(4-aminophenoxy)propan-2-ol

A mixture of ethyl 2-piperazinylbenzoate monoacetate (7.24 g) as obtained in Reference Example 1, 4-nitrophenyloxirane (4.80 g) as obtained by the same reaction procedure as described in Reference Example 2, dioxane (200 ml), and triethylamine (6.8 ml) is refluxed for 5 hours. This reaction mixture is treated as in Example 1 and the residue is subjected to silica gel chromatography using ethyl acetate to provide 3-[4-(2-carbethoxyphenyl)piperazinyl]-1(4-nitrophenoxy)propan-2-ol (2.5 g) as yellow oil. This product (2.0 g) is hydrolyzed and treated as in Example 1 and the residue is converted to the hydrochloride and recrystallized from ethanol-ethyl acetate to provide 3-[4-(2-carboxyphenyl)piperazinyl]-1-(4-nitrophenoxy)propan-2-ol. 2HCl melting at 175° C.–178° C. (1.0 g). This compound (1.0 g) is subjected to catalytic reduction using 10% palladium-on-carbon in dioxane (50 ml)-water (50 ml). After the solvent is distilled off, the residue is recrystallized from acetone to provide the title compound melting at 260° C.–263° C. (0.8 g).

Elemental analysis for $C_{20}H_{25}N_3O_4 \cdot 2HCl \cdot 1.25H_2O$; Calcd. (%): C, 51.45; H, 6.37; N, 9.00; Found (%): C, 51.24; H, 6.03; N, 8.82

Example 10

3-[4-(2-carboxyphenyl)piperazinyl]-1-(3-tert-butyl-4-hydroxyphenoxy)propan-2-ol A mixture of ethyl 2-piperazinylbenzoate monoacetate 1.47 g) as obtained in Reference Example 1, 4-benzyloxy-3-tert-butyl-phenoxyoxirane (1.56 g) as obtained by the same reaction procedure as described in Reference Example 2, dioxane (100 ml), and triethylamine (1.4 ml) is refluxed for 5 hours. This reaction mixture is treated as in Example 1 and the residue is subjected to silica gel chromatography using ethyl acetate-hexane (1:2) to provide 3-[4-(2-carbethoxyphenyl)piperazinyl]-1-(4-benzyloxy-3-tert-butylphenoxy)propan-2-ol (1.32 g) as light-yellow oil. This product (1.32 g) is hydrolyzed and treated as in Example 1 and the residue is converted to the hydrochloride and crystallized from acetone to provide 3-[4-(2-carboxyphenyl)piperazinyl]-1-(4-benzyloxy-3-tert-butylphenoxy)propan-2-ol (1.10 g). This compound (1.10 g) is subjected to catalytic reduction using 10% palladium-on-carbon in dioxane (50 ml)-water (50 ml) and recrystallized from methanol-acetone to provide the title compound melting at 236° C.–238° C. (0.4 g).

Elemental analysis for $C_{24}H_{32}N_2O_5 \cdot HCl \cdot 0.75H_2O$; Calcd. (%): C, 60.24; H, 7.27; N, 5.85; Found (%): C, 60.45; H, 7.17; N, 5.88

Example 11

Effect of the compound of the invention on the passive cutaneous anaphylactic (PCA) reaction of the rat palpebra The effect of the compound of the invention on rat palpebral PCA reaction was investigated.

(Test substances)
(1) 3-[4-(2-Carboxyphenyl)piperazinyl]-1-(2-tert-butyl-4-methoxyphenoxy)propan-2-ol (Compound of Example 1)
(2) 3-[4-(2-Carboxyphenyl)piperazinyl]-1-(1H-indol-4-yloxy)propan-2-ol (Compound of Example 5)

(Method)

Male Wistar rats weighing about 120 g were purchased from Japan SLC for the experiment.

Using a microsyringe, 25 µl of antiserum (32-fold dilution) was injected beneath the palpebral conjunctiva of the right eye of rats under pentobarbital anesthesia. Forty-eight (48) hours after injection of antiserum, a mixture of 2% chicken egg albumin and 1% Evans blue, 5 ml/kg, was administered into the tail vein to induce PCA reaction. Thirty (30) minutes after induction, the rat was sacrificed and the stained portion of the palpebral conjunctiva of the right eye was excised. The dye was extracted into 5 ml of formamide, and the amount of the dye was determined at 625 nm.

The test substance, 100 mg/5 ml/kg, was administered orally 60 minutes prior to induction of PCA reaction.

As a negative control, 5 ml/kg of 0.5% carboxymethyl-cellulose (CMC) was administered orally. As a positive control, 100 mg/5 ml/kg of diphenhydramine hydrochloride, a commercial antihistaminic, was administered orally.

(Results)

The results are shown in Tables 1 and 2. It is apparent from these results that the compound of the invention is of value as an antiallergic agent.

TABLE 1

Effect of the compound of the invention on rat palpebral PCA reaction

| Group | Absorbance | Degree of Inhibition (%) |
|---|---|---|
| Negative control | 0.662 ± 0.112 | — |
| Compound of Example 1 | 0.299 ± 0.056 *2 | 54.8 |
| Diphenhydramine HCl | 0.413 ± 0.126 *1 | 37.6 |

Each figure represents mean ± SD (n = 5).
Significant difference from negative control:
*1; p < 0.05, *2; p < 0.001.
Student's t-test

TABLE 2

Effect of the compound of the invention on rat palpebral PCA reaction

| Group | Absorbance | Degree of Inhibition (%) |
|---|---|---|
| Negative control | 0.486 ± 0.093 | — |
| Compound of Example 5 | 0.276 ± 0.048 *1 | 43.2 |

Each figure represents mean ± SD (n = 6).
Significant difference from negative control:
*1; p < 0.001.
Student's t-test Formulation Example 1

Oral Tablets

| | |
|---|---|
| Compound of Example 1 | 30 mg |
| Lactose | 80 mg |
| Starch | 17 mg |
| Magnesium stearate | 3 mg |

Formulation Example 2

Eye-drops

| | |
|---|---|
| Compound of Example 5 | 100 mg |
| Boric acid | 700 mg |
| Borax | 400 mg |
| Sodium chloride | 500 mg |
| Methyl p-hydroxybenzoate | 26 mg |
| Propyl p-hydroxybenzoate | 14 mg |
| Sterilized purified water | to make 100 ml |

The piperazine derivative, inclusive of its salt, of the present invention has potent antiallergic activity and can therefore be used with advantage in the treatment of various allergic diseases.

What is claimed is:

1. A piperazine derivative of the following formula (I) or a pharmacologically acceptable salt thereof

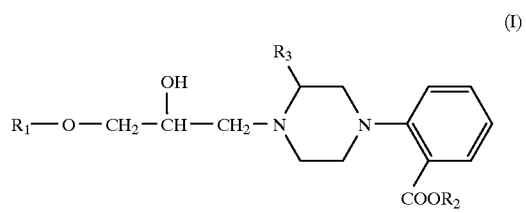

wherein
R$_1$ represents 2-tert-butyl-4-methoxyphenyl, 3-tert-butyl-4-hydroxyphenyl, 3,4-methylenedioxyphenyl, naphthalene ring, indole ring or chroman ring which rings may be substituted by lower alkyl lower alkoxy and/or hydroxy; and
R$_2$ and R$_3$ independently represent hydrogen or lower alkyl.

2. The piperazine derivative of claim 1 which is 3-[4-(2-carbethoxyphenyl)piperazinyl]-1-(2-tert-butyl-4-methoxyphenoxy)propan-2-ol or a pharmacologically acceptable salt thereof.

3. The piperazine derivative of claim 1 which is 3-[4-(2-carboxyphenyl)piperazinyl]-1-(2-tert-butyl-4-methoxyphenoxy)propan-2-ol or a pharmacologically acceptable salt thereof.

4. The piperazine derivative of claim 1 which is 3-[4-(2-carbethoxyphenyl)piperazinyl]-1-(1-naphthyloxy)propan-2-ol or a pharmacologically acceptable salt thereof.

5. The piperazine derivative of claim 1 which is 3-[4-(2-carboxyphenyl)piperazinyl]-1-(1-naphthyloxy)propan-2-ol or a pharmacologically acceptable salt thereof.

6. The piperazine derivative of claim 1 which is 3-[4-(2-carbethoxyphenyl)piperazinyl]-1-(1H-indol-4-yloxy)propan-2-ol or a pharmacologically acceptable salt thereof.

7. The piperazine derivative of claim 1 which is 3-[4-(2-carboxyphenyl)piperazinyl]-1-(1H-indol-4-yloxy)propan-2-ol or a pharmacologically acceptable salt thereof.

8. The piperazine derivative of claim 1 which is 3-[4-(2-carbethoxyphenyl)-2-methylpiperazinyl]-1-(2-tert-butyl-4-methoxyphenoxy)propan-2-ol or a pharmacologically acceptable salt thereof.

9. The piperazine derivative of claim 1 which is 3-[4-(2-carboxyphenyl)-2-methylpiperazinyl]-1-(2-tert-butyl-4-methoxyphenoxy)propan-2-ol or a pharmacologically acceptable salt thereof.

10. The piperazine derivative of claim 1 which is 3-[4-(2-carbethoxyphenyl)piperazinyl]-1-(3,4-methylenedioxyphenoxy)propan-2-ol or a pharmacologically acceptable salt thereof.

11. The piperazine derivative of claim 1 which is 3-[4-(2-carboxyphenyl)piperazinyl]-1(3,4-methylenedioxyphenoxy)propan-2-ol or a pharmacologically acceptable salt thereof.

12. The piperazine derivative of claim 1 which is 3-[4-(2-carbethoxyphenyl)piperazinyl]-1-(α-tocopherol-6-yl)propan-2-ol or a pharmacologically acceptable salt thereof.

13. The piperazine derivative of claim 1 which is 3-[4-(2-carboxyphenyl)piperazinyl]-1-(α-tocopherol-6-yl)propan-2-ol or a pharmacologically acceptable salt thereof.

14. The piperazine derivative of claim 1 which is 3-[4-(2-carboxyphenyl)piperazinyl]-1-(3-tert-butyl-4-hydroxyphenoxy)propan-2-ol or a pharmacologically acceptable salt thereof.

15. A process for producing a piperazine derivative or a pharmacologically acceptable salt thereof as claimed in claim 1 which comprises subjecting an 2,3-epoxypropanol derivative of the following formula (II) (wherein $R_1$ is as defined in claim 1) and a 4-(2-carbalokoxyphenyl) piperazine of the following formula (III) (wherein $R_2$ and $R_3$ are defined in claim 1) to thermal condensation reaction or by subjecting the resulting compound further to hydrolysis reaction.

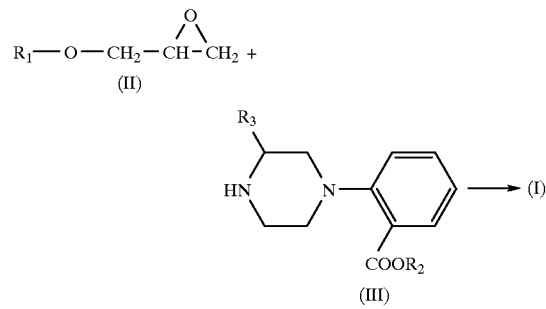

16. A pharmaceutical composition comprising an effective amount of a piperazine derivative or a pharmacologically acceptable salt thereof as claimed in claim 1 as an active ingredient and a pharmaceutically acceptable carrier therefor.

17. An antiallergic composition comprising an antiallergic effective amount of a piperazine derivative or a pharmacologically acceptable salt thereof as claimed in claim 1 as an active ingredient and a pharmaceutically acceptable carrier therefor.

* * * * *